United States Patent [19]

Kawano

[11] Patent Number: 5,170,669
[45] Date of Patent: Dec. 15, 1992

[54] HAIR NATURE MEASURING INSTRUMENT
[75] Inventor: Junichi Kawano, Sakura, Japan
[73] Assignee: Kao Corporation, Tokyo, Japan
[21] Appl. No.: 675,955
[22] Filed: Mar. 27, 1991
[30] Foreign Application Priority Data
  Apr. 11, 1990 [JP]  Japan .................. 2-95497
[51] Int. Cl.⁵ .................. G01N 3/26; G01N 3/40
[52] U.S. Cl. ........................ 73/847; 73/78; 132/213
[58] Field of Search ............... 73/866, 78, 80, 847, 73/848, 160; 128/630; 132/213

[56] References Cited

U.S. PATENT DOCUMENTS

| | | | |
|---|---|---|---|
| 496,191 | 2/1892 | Sooshny | 132/213 |
| 2,765,655 | 10/1956 | Scott | 73/847 X |
| 3,015,336 | 1/1962 | Coples | 132/213 |
| 3,712,124 | 1/1973 | Lutz | 73/789 |
| 4,022,057 | 5/1977 | Bachman et al. | 73/847 |
| 4,628,742 | 12/1986 | Golding | 73/829 |
| 4,891,974 | 1/1990 | Wasserhaven | 73/847 X |
| 4,958,522 | 9/1990 | McKinley | 73/847 |

FOREIGN PATENT DOCUMENTS

| | | | |
|---|---|---|---|
| 96334 | 2/1898 | Fed. Rep. of Germany | 73/847 |
| 2254992 | 7/1975 | France | 73/847 |
| 28639 | 2/1987 | Japan | 73/847 |
| 789696 | 12/1980 | U.S.S.R. | 73/847 |
| 1179141 | 9/1985 | U.S.S.R. | 73/847 |
| 1504565 | 8/1989 | U.S.S.R. | 73/847 |

Primary Examiner—Tom Noland

[57] ABSTRACT

A hair nature measuring instrument comprises a hair catching portion, a rotational handle portion for rotating the hair catching portion, a rotation transmitting element having a restoring resilient force and interconnecting the hair catching portion and the rotational handle portion, and a grip portion for loosely circumscribing the rotation transmitting element. The nature of hair (hardness) is measured based on a correlation between the amount of rotation of the rotational handle portion and the amount of rotation of the hair catching portion when the hair catching portion already catching hair is rotated by the rotational handle portion.

17 Claims, 1 Drawing Sheet

HAIR NATURE MEASURING INSTRUMENT

BACKGROUND OF THE INVENTION

1. Field of the Invention

This invention relates to a hair nature measuring instrument and particularly to a hair nature measuring instrument capable of measuring the nature of human hair, especially the hardness thereof in a simple manner and with high accuracy but without cutting hair from the user's head.

2. Description of the Prior Art

It is a very important factor for a person who is going to set or arrange his or her hair or for a person who is going to have his or her hair permanently waved or dyed to know the nature of the hair, especially the hardness thereof beforehand in order to select a suitable cosmetic or a suitable chemical lotion, or to treat the hair properly. The hardness of hair has heretofore been measured (or checked), in many cases, by means of hand touch or the like based on the measurer's (user's) own experience.

When it was necessary that the hardness of hair is checked with high accuracy, hair was often cut from the head and taken to a laboratory or the like in order to have the hair measured using a special instrument.

However, it was impossible to obtain a concrete measured value when the hardness of hair was measured by means of hand touch. Besides, since the results of measurement were different when measurerers were different and when various other factors were different, it was absolutely impossible to quantify the measured values according to the above-mentioned measuring method.

If the hardness of hair is measured using a special instrument in a laboratory or the like, a measured value having a certain degree of accuracy can be obtained. In this case, however, a considerable amount of time and expense is required, and it is practically impossible to measure the hardness of hair in a shop or at home using such a conventional device with ease and with high accuracy.

Because of the above-mentioned reasons, proper treatment was not necessarily made to the hair to the full satisfaction of the user when hair was set or arranged in a barber's shop or in a beauty salon. Also, because of the above-mentioned reasons, it was difficult for the user of hair cosmetics to obtain an appropriate advice from an expert.

SUMMARY OF THE INVENTION

An object of the present invention is to provide a hair nature measuring instrument which is capable of measuring the nature of human hair, especially the hardness thereof in a simple manner and with high accuracy but without cutting hair from the user's head and which is simple in structure and inexpensive.

To achieve the above object, according to the present invention, there is provided a hair nature measuring instrument comprising a hair catching portion, a rotational handle portion for rotating the hair catching portion, a rotation transmitting element having a restoring resilient force and interconnecting the hair catching portion and the rotational handle portion, and a grip portion for loosely circumscribing the rotation transmitting element, the nature of hair (hardness) being measured based on a correlation between the amount of rotation of the rotational handle portion and the amount of rotation of the hair catching portion when the hair catching portion already catching hair is rotated by the rotational handle portion.

According to a hair nature measuring instrument of the present invention, when the rotational handle portion is rotated by a predetermined angle with one hand (right hand) after the hair catching portion is inserted into the human hair while grasping the grip portion with the other hand (left hand), rotation of the rotational handle portion is transmitted to the hair catching portion through the rotation transmitting element, and as a result, the hair catching portion is also rotated. Accordingly, the hair (the hair caught in a space of a fork member provided that the hair nature measuring instrument of this embodiment is used) caught by the hair catching portion receives a force directing in the winding direction with respect to the hair catching portion and as a result, the hair resists against the rotation of the hair catching portion. At that time, the larger the resistance of the hair is (the harder the hair is, i.e., the larger the hardness of the hair is), the smaller the value of "amount of rotation of the hair catching portion"/"amount of rotation of the rotational handle portion" becomes. On the contrary, the smaller the resistance of the hair is (the softer the hair is, i.e., the smaller the hardness of the hair is), the larger the value of "amount of rotation of the hair catching portion"/"amount of rotation of the rotational handle portion" becomes.

Accordingly, the hair nature measuring instrument of the present invention is capable of measuring the nature of human hair, especially the hardness thereof in a simple manner and with high accuracy but without cutting hair from the measurer's head. Moreover, it is simple in structure and inexpensive, thus enabling to be used advantageously in such a store as to sell cosmetics, in a barber's shop or in a beauty salon, or at home.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE EMBODIMENT

Figure 1:
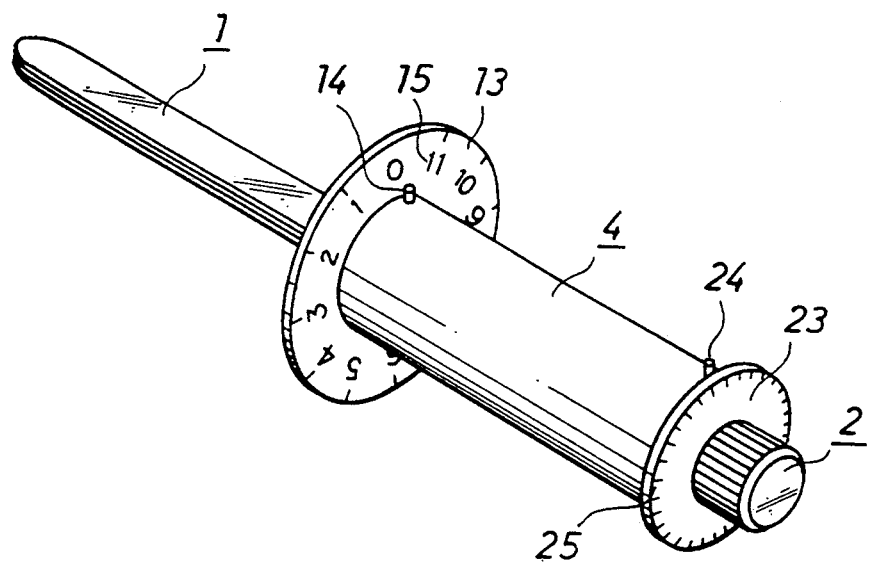
FIG. 1 is a perspective view showing one embodiment of a hair nature measuring instrument of the present invention.
Figure 2:
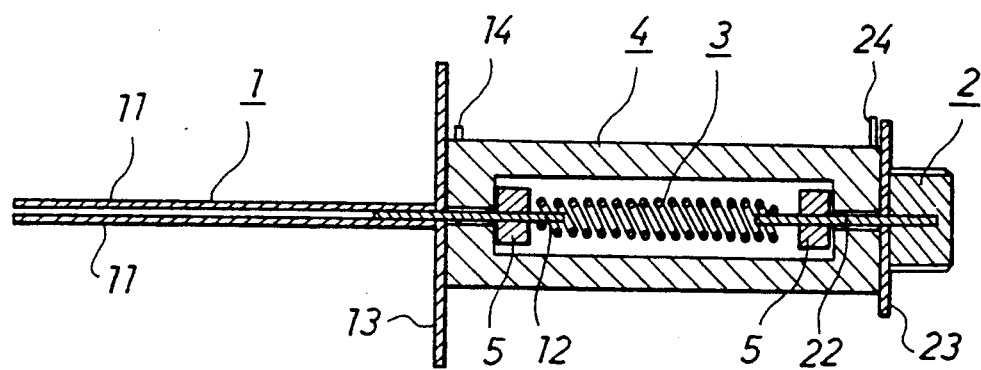
FIG. 2 is a vertical sectional view thereof.

A hair nature measuring instrument of the present invention will now be described in detail with reference to one embodiment depicted in the drawings.

A hair nature measuring instrument of the present invention includes a hair catching portion 1, a rotational handle portion 2 for rotating the hair catching portion 1, a rotation transmitting element (coil spring) 3 interconnecting the hair catching portion 1 and the rotational handle portion 2, and a grip portion 4 for loosely circumscribing the coil spring 3.

The hair catching portion 1 is formed of a fork member having a pair of elongated flat plates providing with a space therebetween and fixed to one end of the grip portion 1 with front end portions thereof released. A rotational shaft 12 is integrally formed with a central portion of a basic portion of the fork member. The rotational shaft 12 is connected and fixed to one end of the coil spring 3. Another rotational shaft 22 is also integrally formed with a central portion of the rotational handle portion 2. The rotational shaft 22 is connected and fixed to the other end of the coil spring 3.

The grip portion 4 is grasped by hand when the hair nature measuring instrument is in use. The coil spring 3 is loosely circumscribed by the grip portion 4 in order not to prevent the spring 3 from being rotated together with the hair catching portion 1 and the rotational handle portion 2 which are interconnected by the spring 3.

The hair catching portion 1 and the rotational handle portion 2 are respectively integrally provided with circular disk-shaped rotation amount indicating portions 13 and 23 such that the centers of the portions 13 and 23 are in alignment with the centers of the respective rotational shafts 12 and 22. Indicating needle portions 14 and 24 are disposed to the outer surfaces of front (hair catching portion 1 side) and rear (rotational handle portion 2 side) end portions of the grip portion 4. Furthermore, the rotation amount indicating portions 13 and 23 are provided with graduations (marks) 15 and 25 respectively indicating the amount of fluctuation (amount of rotation) of the hair catching portion 1 caused by rotation of the rotational handle portion 2 and the amount of rotation (angle of rotation) of the rotational handle portion 2 with reference to a positional relation with the grip portion 4 at the start of use of the hair nature measuring instrument. Arrangement being such that the amounts of rotation (angles of rotation) of the hair catching portion 1 and the rotational handle portion 2 can be read from the graduations 15 and 25 and from the indicating needle portions 14 and 24.

In order to facilitate an easy handling of the hair nature measuring instrument, the hair nature measuring instrument of the embodiment is provided with a stopper (not shown). Arrangement being such that when the rotational handle portion 2 is rotated counterclockwise in use, rotation of the rotational handle portion 2 is stopped by the stopper in a position where the indicating needles 14 and 24 indicate a base point (0 point) of the graduations 15; 25 of the rotation indicating portions 13 and 23.

In the drawings, the numerals 5, 5 denote anti-rattle members fixed to the rotational shafts 12 and 22 so that rotation of the rotational handle portion 2 is smoothly transmitted to the hair catching portion 1 through the rotation transmitting element 3.

Next, one method for the use of a hair nature measuring instrument of the present invention will be described.

First, after the rotational handle portion 2 is rotated counterclockwise until it is stopped by the stopper, the grip portion 4 is grasped by one hand (left hand) and the hair catching portion (fork member) 1 is inserted into the human hair. Under the foregoing circumstance, a predetermined amount of hair is sandwiched between the flat plates 11, 11 of the fork member 1, and the indicating needle portions 14 and 24 respectively indicate 0 point (amount of rotation: 0) of the graduations 15 and 25 in the rotation indicating portions 13 and 23.

Next, the rotational handle portion 2 is rotated clockwise by the other hand (right hand). In this case, the amount of rotation (angle of rotation) of the rotational handle portion 2 is usually stipulated on the graduations 25 before hand and the rotational handle portion 2 is rotated until the stipulated position on the graduations 25 is brought into coincident with the position of the indicating needle 24.

When the rotational handle portion 2 is rotated by a predetermined angle of rotation, the rotation of the rotational handle portion 2 is transmitted to the hair catching portion 1 through the coil spring 3 to rotate the hair catching portion 1. As a result, the hair caught in the space of the fork member 1 receives a force directing in the winding direction with respect to the fork member 1.

As a consequence, the hair resists against the rotation of the fork member 1. At that time, the larger the resistance of the hair is (the harder the hair is, i.e., the larger the hardness of the hair is), the smaller the amount of rotation of the hair catching portion becomes. On the contrary, the smaller the resistance of the hair is (the softer the hair is, i.e., the smaller the hardness of the hair is), the larger the amount of rotation of the hair catching portion 1 (amount of rotation of the rotational handle portion) becomes.

Thereafter, the amount of rotation (angle of rotation) of the fork member 1 is read from the graduations 15 of the rotation amount indicating portion 13 when the rotational handle portion 2 is rotated by a predetermined amount.

By reading the amount of rotation of the fork member (hair catching portion) in the manner as mentioned above, the hardness of the hair can be read from a relation between the read value and the amount of rotation of the rotational handle portion 2.

That is, if the hardness of a plurality of hairs is measured by the hair nature measuring instrument of the present invention beforehand in the manner as mentioned above and if a table showing, among other things, a correlation between the amount of rotation of the rotational handle portion and the amount of rotation of the hair catching portion based on such measured values and a relation between said relation and the hardness of the hair is prepared, the hardness of hair can immediately be known by reading the amount of rotation of the hair catching portion in the manner as mentioned above and referring to the table to obtain a relation between the read value and the amount of rotation of the rotational handle portion at that time.

It is noted that the hair nature measuring instrument of the present invention is not limited to the above embodiment and that it can be changed or modified without departing from the gist of the invention. For example, the configuration, etc. of the hair catching portion can be changed in accordance with necessity. Similarly, the rotation transmitting element is not limited to the coil spring, either. Any other means can be served as the rotation transmitting element as long as they have a restoring resilient force and the rotation of the rotational handle portion can be transmitted to the hair catching portion to rotate the hair catching portion.

Although the rotation amount indicating portion is provided with graduations in the above embodiment, marks, etc. showing a five rank evaluation such as, for example, "hard", "a little hard", "a little soft" and "soft" may be affixed in the form of a circular graph instead of the graduations. By doing so, it can be immediately known which rank the hardness of the hair belongs to. The configuration of the hair catching portion is not limited to that of the embodiment, either. However, the hair catching portion is preferably formed in a structure wherein hair can surely be caught by the hair catching portion when the rotational handle portion is rotated as in the fork member of the embodiment.

Furthermore, it may be designed such that the rotation amount indicating portion of the rotational handle portion is integrally formed with the grip portion, the rotation indicating portion is freed from the rotational handle portion and the indicating needle portion on the side of the rotational handle portion is disposed to the rotational handle portion itself. In addition, for example, a weight may be provided to a part of the rotation indicating portion of the hair catching portion so that a positional correlation among the hair catching portion, the rotational handle portion and the grip portion is automatically returned to a predetermined state at least at the start of use.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A hair nature measuring instrument comprising a hair catching portion, a rotational handle portion for rotating said hair catching portion, a rotation transmitting element having a restoring resilient force and interconnecting said hair catching portion and said rotational handle portion, and a grip portion for loosely circumscribing said rotation transmitting element, the nature of hair being measured based on a correlation between amount of rotation of said rotational handle portion and amount of rotation of said hair catching portion when said hair catching portion already catching hair is rotated by said rotational handle portion.

2. The hair nature measuring instrument as claimed in claim 1, wherein rotation amount indicating portions are integrally formed with said hair catching portion and said rotational handle portion, respectively.

3. The hair nature measuring instrument as claimed in claim 2, wherein each rotation amount indicating portion includes at least one of graduations and marks corresponding to an amount of fluctuation in positional relation with said grip portion.

4. The hair nature measuring instrument as claimed in claim 1, wherein hardness of the hair is measured by the instrument without a need for cutting of the hair, the rotation transmitting element and the grip portion being located between the hair catching portion and the rotational handle portion.

5. The hair nature measuring instrument as claimed in claim 1, wherein the hair catching portion comprises a pair of flat plates operatively connected to the rotation transmitting element, the flat plates being rotatable about a longitudinal axis, the longitudinal axis extending through the rotation transmitting element and the rotational handle portion.

6. The hair nature measuring instrument as claimed in claim 5, wherein the rotation transmitting element comprises a coil spring.

7. The hair nature measuring instrument as claimed in claim 6, wherein the coil spring is housed within the grip portion and wherein rotation of the handle portion with respect to the grip portion transmits a rotational force through the coil spring to the hair catching portion.

8. The hair nature measuring instrument as claimed in claim 1, further comprising means for determining hardness of hair based on the correlation between the amount of rotation of the rotational handle portion and the amount of rotation of said hair catching portion when said hair catching portion means already catching hair is rotated, the means comprises at least one indicator for indicating the amount of rotation of one of said rotational handle portion and said hair catching portion.

9. A hair nature measuring instrument comprising:
means for gripping hair;
a rotational handle portion for rotation said means for gripping hair;
rotation transmitting means for interconnecting the rotational handle portion and the means for gripping hair, the rotation transmitting means having a restoring resilient force;
a grip portion positioned between the means for gripping hair and the rotational handle portion, the rotational handle portion being rotatable with respect to the grip; and
means for measuring nature of the hair gripped by the means for gripping hair, the measuring being based on a correlation between an amount of rotation of said rotational handle portion and an amount of rotation of said means for gripping when said means for gripping hair is rotated by said rotational handle portion.

10. The hair nature measuring instrument as claimed in claim 9, wherein the means for measuring measures hardness of hair without a need for cutting of the hair, the means for measuring comprising at least one indicator for indicating the amount of rotation of one of said rotational handle portion and said means for gripping hair.

11. The hair nature measuring instrument as claimed in claim 9, wherein the means for measuring measures hardness of hair without a need for cutting of the hair, the means for measuring comprising an indicator for indicating the amount of rotation of said rotational handle portion and an indicator for indicating the amount of rotation of said means for gripping hair.

12. The hair nature measuring instrument as claimed in claim 9, wherein the means for measuring comprises rotation amount indicating portions integrally formed with said means for gripping hair with said rotational handle portion, respectively.

13. The hair nature measuring instrument as claimed in claim 12, wherein each rotation amount indicating portion includes at least one of graduations and marks corresponding to an amount of fluctuation in positional relation with said grip portion.

14. The hair nature measuring instrument as claimed in claim 9, wherein hardness of the hair is measured by the means for measuring, the rotation transmitting means and the grip portion being located between the means for gripping hair and the rotational handle portion.

15. The hair nature measuring instrument as claimed in claim 9, wherein the means for gripping hair comprises a pair of flat plates operatively connected to the rotation transmitting means, the flat plates being rotatable about a longitudinal axis.

16. The hair nature measuring instrument as claimed in claim 15, wherein the rotation transmitting means comprises a coil spring, the longitudinal axis about which the flat plates rotate passing through the coil spring.

17. The hair nature measuring instrument as claimed in claim 16, wherein the coil spring is housed within the grip portion and wherein rotation of the handle portion with respect to the grip portion transmits a rotational force through the coil spring to the hair catching portion.

* * * * *